(12) United States Patent
Oguro

(10) Patent No.: US 9,448,247 B2
(45) Date of Patent: Sep. 20, 2016

(54) BLOOD SAMPLE PROCESSING APPARATUS AND BLOOD SAMPLE PROCESSING METHOD

(75) Inventor: Masahiko Oguro, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 407 days.

(21) Appl. No.: 12/891,436

(22) Filed: Sep. 27, 2010

(65) Prior Publication Data

US 2011/0076668 A1   Mar. 31, 2011

(30) Foreign Application Priority Data

Sep. 30, 2009   (JP) ................................ 2009-227463

(51) Int. Cl.
| | | |
|---|---|---|
| *C12M 3/00* | (2006.01) | |
| *C12N 5/078* | (2010.01) | |
| *G01N 35/04* | (2006.01) | |
| *G01N 35/02* | (2006.01) | |
| *B01F 11/00* | (2006.01) | |

(52) U.S. Cl.
CPC ........... *G01N 35/04* (2013.01); *B01F 11/0008* (2013.01); *B01F 11/0017* (2013.01); *G01N 35/026* (2013.01)

(58) Field of Classification Search
None
See application file for complete search history.

(56) References Cited

U.S. PATENT DOCUMENTS

| | | | | | |
|---|---|---|---|---|---|
| 3,625,485 | A | * | 12/1971 | Adler | 366/216 |
| 4,957,373 | A | * | 9/1990 | Derksen et al. | 366/197 |
| 5,731,513 | A | * | 3/1998 | Bull | 73/61.66 |
| 6,135,172 | A | * | 10/2000 | Fere et al. | 141/329 |
| 2005/0180884 | A1 | * | 8/2005 | Itoh | 422/63 |
| 2005/0196320 | A1 | * | 9/2005 | Veiner et al. | 422/63 |
| 2007/0048185 | A1 | * | 3/2007 | Dupoteau et al. | 422/68.1 |
| 2007/0110627 | A1 | | 5/2007 | Nagai et al. | |

FOREIGN PATENT DOCUMENTS

| | | |
|---|---|---|
| JP | 2007-503580 | 2/2007 |
| JP | 2011-75417 | 4/2011 |

* cited by examiner

*Primary Examiner* — Jill Warden
*Assistant Examiner* — Benjamin Whatley
(74) *Attorney, Agent, or Firm* — Brinks Gilson & Lione

(57) ABSTRACT

A blood sample processing apparatus including: a container holder securing a sample container that contains a blood sample, the sample container having a lid, the container holder coupled to a rotation driver that longitudinally rotates the sample container; and a controller that commands the rotation driver to repeatedly perform an inclining-stirring operation that includes a first process and a second process, wherein in the first process, the sample container is initially held in an upright position by the container holder and then rotated to an inclined position, and in the second process, the inclined sample container is returned to the upright position, and wherein in a final inclining-stirring operation, the second process is carried out for a longer time than previous second processes.

12 Claims, 14 Drawing Sheets

BLOOD SAMPLE PROCESSING APPARATUS AND BLOOD SAMPLE PROCESSING METHOD

RELATED APPLICATIONS

This application claims priority under 35 U.S.C. §119 to Japanese Patent Application No. 2009-227463 filed on Sep. 30, 2009, the entire content of which is hereby incorporated by reference.

FIELD OF THE INVENTION

The present invention relates to a blood sample processing apparatus and a blood sample processing method.

BACKGROUND OF THE INVENTION

Conventionally, blood sample processing apparatuses have been known in which an aspiration tube penetrates a lid (cap) for sealing a specimen container to aspirate the blood sample in the specimen container and the aspirated blood sample is processed.

Among such blood sample processing apparatuses, there is an apparatus which repeatedly performs an inclining-stirring operation, in which a specimen container held in an upright state is rotated to be in an inclining state such that a bottom portion of the specimen container is positioned higher than a lid, and then is returned to its original upright state, and then which aspirates a blood sample to carry out analysis.

For example, a sample analysis apparatus described in U.S. Patent Publication No. 2007/110627 is provided with a hand member for holding a specimen container and a driver for rotating the hand member, and performs an inclining-stirring operation of the specimen container by rotating the hand member holding the specimen container before aspirating a blood sample from the specimen container by an aspiration tube.

The pressure inside the specimen container is higher than the pressure of the atmosphere, therefore, in the blood sample processing apparatus which performs such an inclining-stirring operation, the blood sample may be aspirated after opening the inside of the specimen container to the atmosphere in order to secure the quantitative precision in aspirating a blood sample by the aspiration tube.

The opening to the atmosphere is performed by various methods, and for example, there is an apparatus which uses an aspiration tube having a groove extending in a longitudinal direction in an outer circumferential surface thereof to open the inside of a specimen container to the atmosphere before aspirating a blood sample by the aspiration tube. In such an apparatus, when the aspiration tube penetrates the lid of the specimen container, the inside of the specimen container is opened to the air via the groove and thus the inside of the specimen container can be opened to the atmosphere.

However, when performing an inclining-stirring operation of a specimen container as in the sample analysis apparatus described in U.S. Patent Publication No. 2007/110627, a blood sample may adhere to the back side of the lid of the specimen container in accordance with the lid type. The pressure in the sealed specimen container is higher than the pressure of the atmosphere as described above. Accordingly, when an aspiration tube having a groove extending in a longitudinal direction in an outer circumferential surface thereof penetrates the lid of the specimen container in a state in which the blood sample adheres to the back side of the lid, the blood sample adhering to the back side of the lid may leak from the upper surface of the lid through the groove of the aspiration tube.

SUMMARY OF THE INVENTION

The scope of the present invention is defined solely by the appended claims, and is not affected to any degree by the statements within this summary.

A first aspect of the present invention is a blood sample processing apparatus comprising: a container holder securing a sample container that contains a blood sample, the sample container having a lid, the container holder coupled to a rotation driver that longitudinally rotates the sample container; a sample aspirator that aspirates the blood sample in the sample container; and a controller that operates the rotation driver and the sample aspirator, wherein the controller commands the rotation driver to repeatedly perform an inclining-stirring operation that includes a first process and a second process, wherein in the first process, the sample container is initially held in an upright position by the container holder and then rotated to an inclined position, and in the second process, the inclined sample container is returned to the upright position, and wherein in a final inclining-stirring operation, the second process is carried out for a longer time than previous second processes, and wherein the controller commands the sample aspirator to aspirate the blood sample in the sample container after the second process of the final inclining-stirring operation.

A second aspect of the present invention is a blood sample processing method comprising: stirring a blood sample in a sample container, the sample container having a lid; and aspirating the blood sample in the sample container after stirring, wherein the stirring comprises an repeated inclining-stirring operation that includes a first process and a second process, wherein in the first process, the sample container is moved from an upright position to an inclined position, and in the second process, the sample container is moved from an inclined position to an upright position, and wherein the second process of a final inclining-stirring operation is performed for a longer time than previous second processes.

A third aspect of the present invention is a blood sample processing apparatus comprising: a container holder securing a sample container that contains a blood sample, the sample container having a lid, the container holder coupled to a rotation driver that longitudinally rotates the sample container while the sample holder holds the sample container; a sample aspirator that aspirates the blood sample in the sample container; and a controller that operates the rotation driver and the sample aspirator, wherein the controller commands the rotation driver to perform an inclining-stirring operation that includes a first process and a second process, wherein in the first process, the sample container is initially held in an upright position by the container holder and then rotated to an inclined position, and in the second process, the inclined sample container is returned to the upright position wherein the second process is carried out for at least about 0.8 seconds, and wherein the controller commands the sample aspirator to aspirate the blood sample in the sample container after performing the second process.

A fourth aspect of the present invention is a blood sample processing method comprising: stirring a blood sample in a sample container, the sample container having a lid; and aspirating the blood sample in the sample container, wherein the stirring comprises an inclining-stirring operation that includes a first process and a second process, wherein in the first process, the sample container is moved from an upright position to an inclined position, and in the second process, the sample container is moved from an inclined position to an upright position, and wherein the second process is performed for at least about 0.8 seconds.

A fifth aspect of the present invention is a blood sample processing apparatus comprising: a container holder securing a sample container that contains a blood sample, the sample container having a lid, the container holder coupled to a rotation driver that longitudinally rotates the sample container; a sample aspirator that aspirated the blood sample in the sample container; and a controller that operates the rotation driver and the sample aspirator, wherein the controller commands the rotation driver to repeatedly perform an inclining-stirring operation that includes a first process and a second process, wherein in the first process, the sample container is initially held in a first state in which a bottom portion of the sample container is positioned lower than the lid and then rotated to a second state in which the bottom portion of the sample container is positioned at least as high as the lid, and wherein in the second process, the sample container is moved from the second state to the first state, wherein the controller commands the rotation driver to perform the second process of a final inclining-stirring operation to be carried out for a longer time than other second processes, and wherein the controller commands the sample aspirator to aspirate the blood sample in the sample container after the second process of the final inclining-stirring operation.

DETAILED DESCRIPTION OF THE PREFERRED EMBODIMENTS

Hereinafter, an embodiment of a blood sample processing apparatus and a blood sample processing method of the present invention will be described in detail with reference to the accompanying drawings.

[Blood Sample Processing Apparatus]

Figure 1:
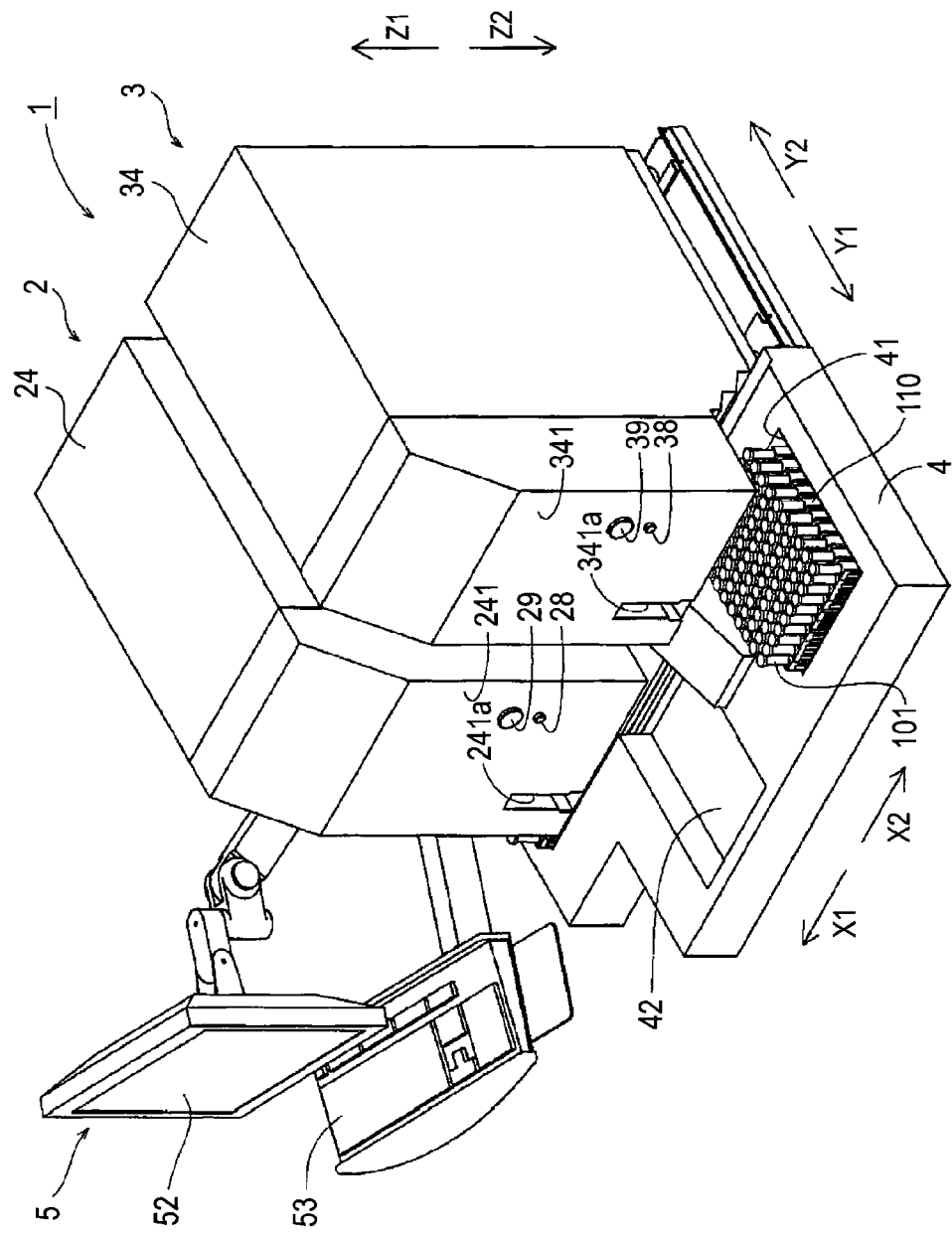
FIG. 1 is a perspective view showing the overall configuration of an embodiment of a blood sample processing apparatus of the present invention.
Figure 2:
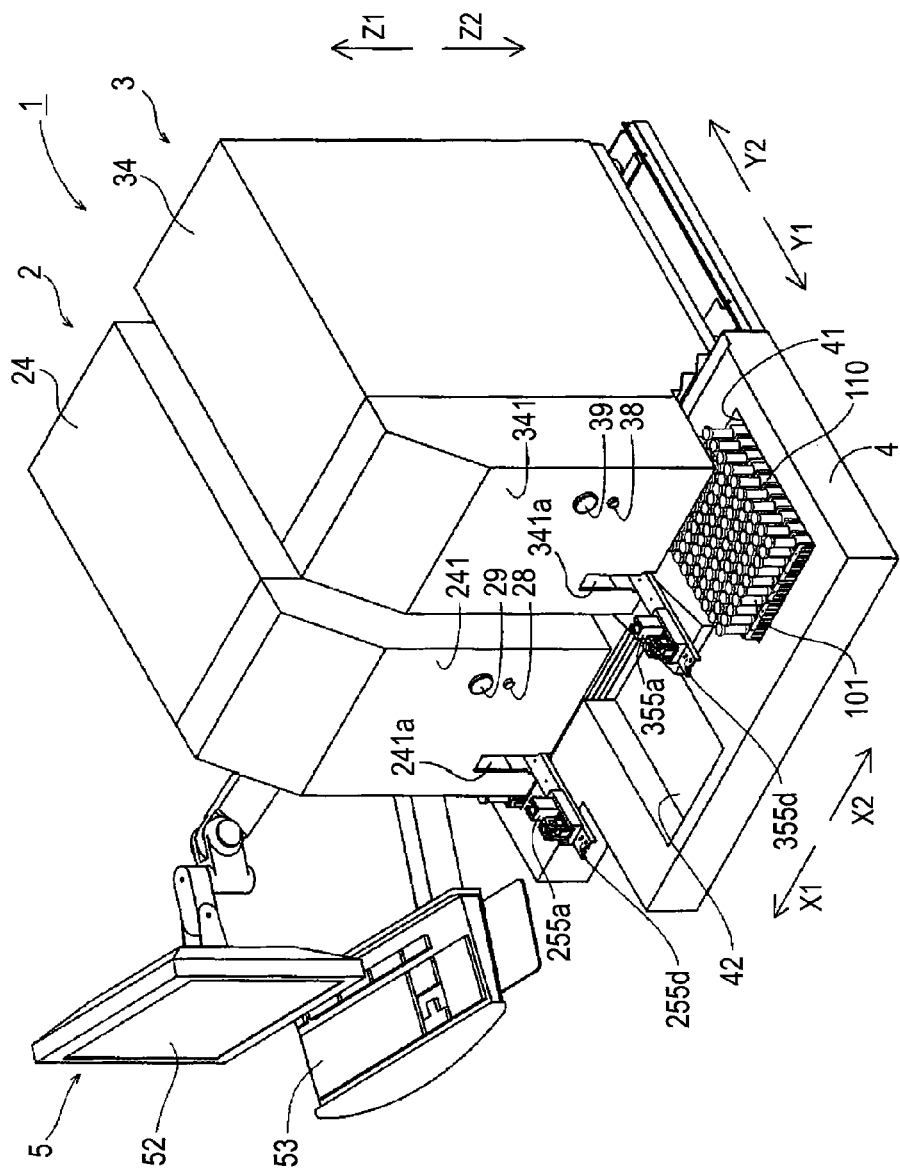
FIG. 2 is a perspective view showing sections in the blood sample processing apparatus shown in FIG. 1 in detail.

First, the overall configuration of a blood sample processing apparatus will be described. A blood sample processing apparatus 1 shown in FIG. 1 is a blood cell counting apparatus for counting the number of blood cells in a blood sample collected from a subject, and as shown in FIGS. 1 and 2, is provided with two measuring units, that is, a first measuring unit 2 and a second measuring unit 3, a specimen transport apparatus (sampler) 4 which is disposed in front of the first measuring unit 2 and the second measuring unit 3 (in a direction of the arrow Y1) and a control apparatus 5 including a personal computer (PC) which is electrically connected to the first measuring unit 2, the second measuring unit 3 and the specimen transport apparatus 4. In addition, the blood sample processing apparatus 1 is connected to a host computer 6 (see FIG. 3) by the control apparatus 5.

Figure 3:
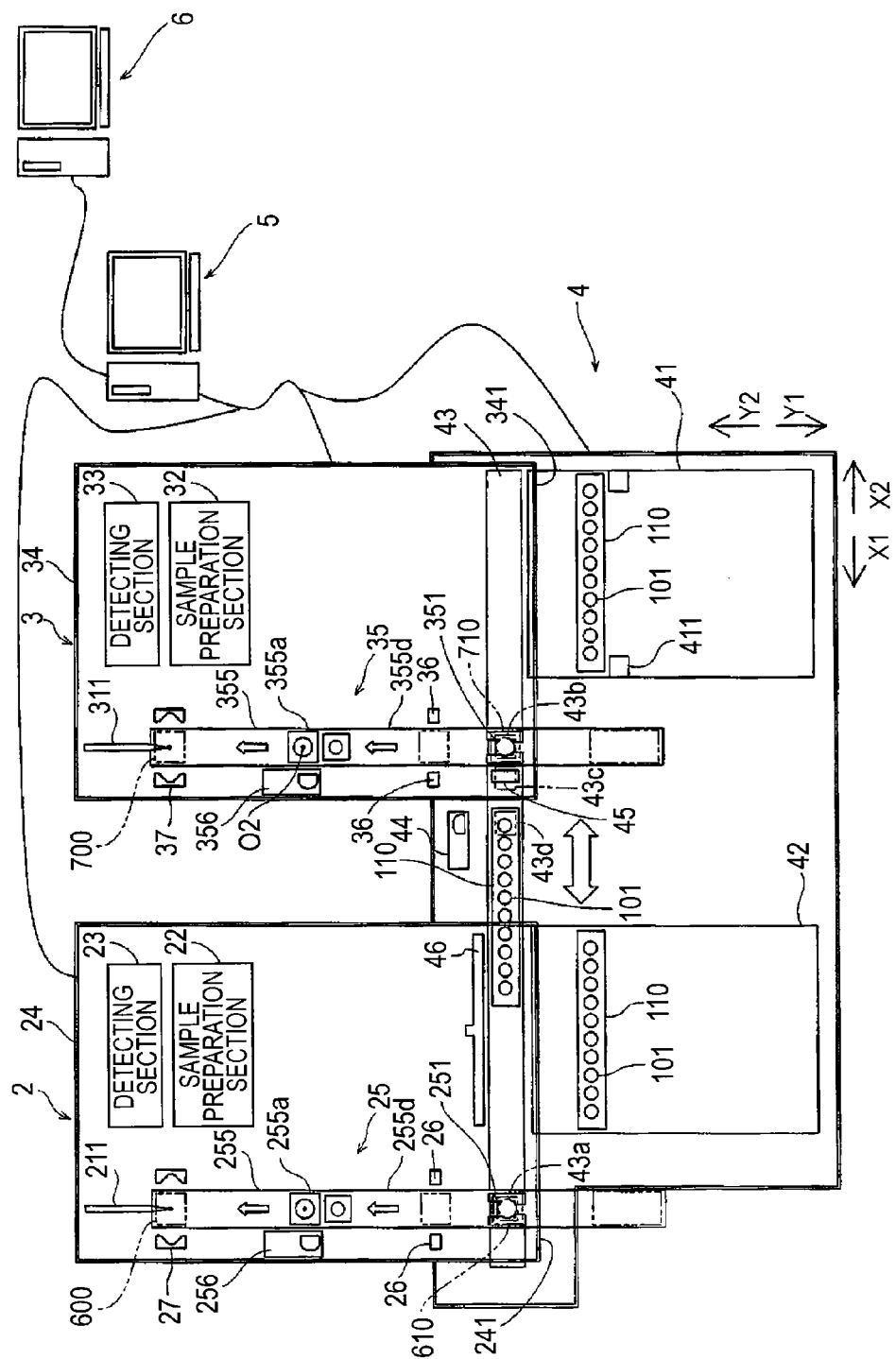
FIG. 3 is a schematic explanatory diagram showing measuring units and a specimen transport apparatus of the blood sample processing apparatus shown in FIG. 1.

In addition, as shown in FIGS. 1 to 3, the first measuring unit 2 and the second measuring unit 3 are substantially the same type of measuring unit and are disposed so as to be adjacent to each other. In greater detail, in this embodiment, the second measuring unit 3 uses the same measurement principle as that of the first measuring unit 2 to measure the same measurement items of a specimen. Further, the second measuring unit 3 also measures the measurement items which are not analyzed by the first measuring unit 2. In addition, as shown in FIG. 3, each of the first measuring unit 2 and the second measuring unit 3 includes a piercer 211 (311) which aspirates blood as a specimen from a specimen container 101, a sample preparation section 22 (32) which prepares a sample for detection from the blood aspirated by the piercer 211 (311), and a detecting section 23 (33) which detects blood cells of the blood from the sample for detection prepared by the sample preparation section 22 (32).

Each of the first measuring unit 2 and the second measuring unit 3 further includes a unit cover 24 (34) which stores the sample preparation section 22 (32) and the like, a specimen container transport section 25 (35) which introduces a specimen container 101 to the inside of the unit cover 24 (34) and transports the specimen container 101 up to a position 600 (700) (see FIG. 3) at which the piercer 211 (311) performs the aspiration, an existence detection section 26 (36) which detects the existence of a specimen container 101 transported to the inside by the specimen container transport section 25 (35), and a chuck section 27 (37) which fixes and holds a specimen container 101 at the aspiration position 600 (700) (see FIG. 3). In addition, as shown in FIGS. 1 and 2, in the respective outer surfaces of front surface sections 241 (341) of the unit covers 24 (34), a specimen setting section opening-closing button 28 (38), a prior specimen measurement start button 29 (39) and an opening section 241a (341a) through which a moving section 255d (355d) (to be described later) of the specimen container transport section 25 (35) passes are provided.

Figure 4:
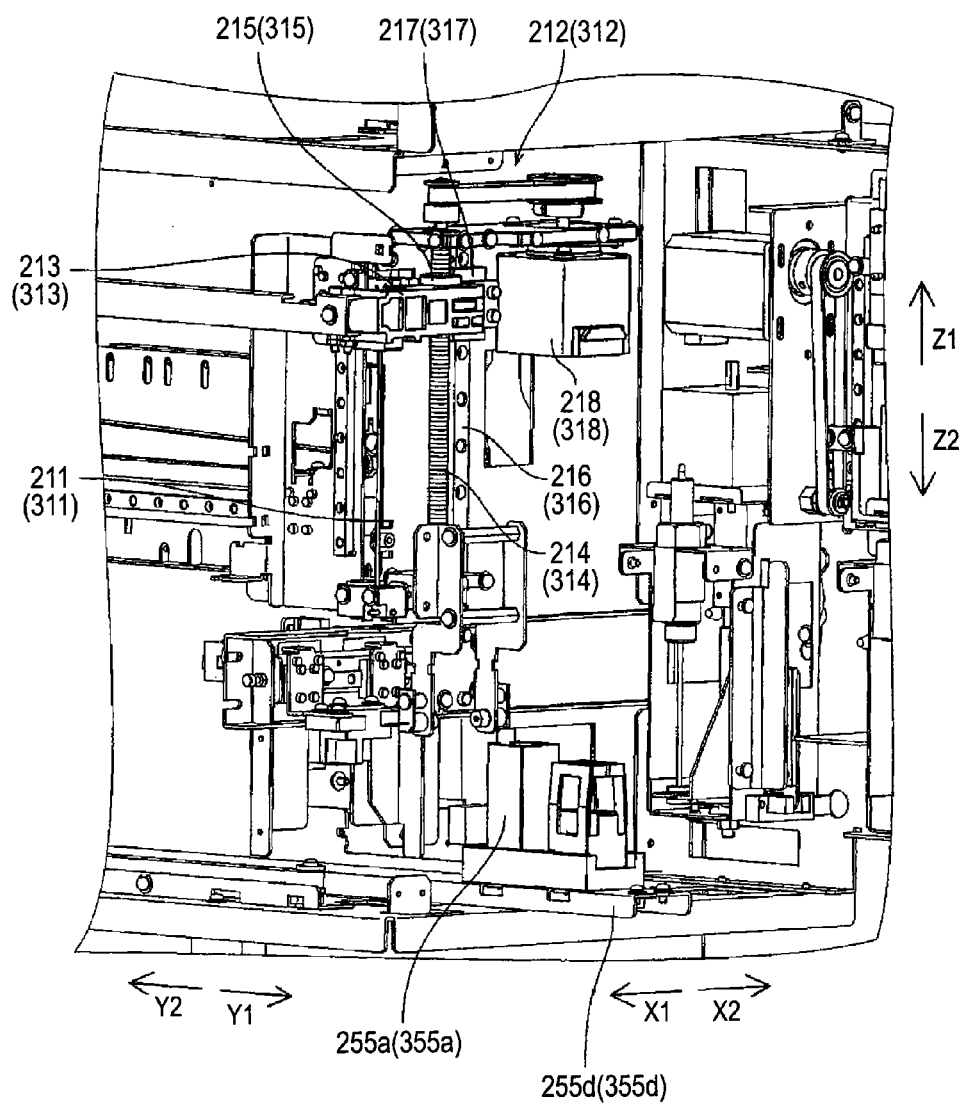
FIG. 4 is a perspective view showing the vicinity of a piercer of the blood sample processing apparatus shown in FIG. 1.
Figure 12:
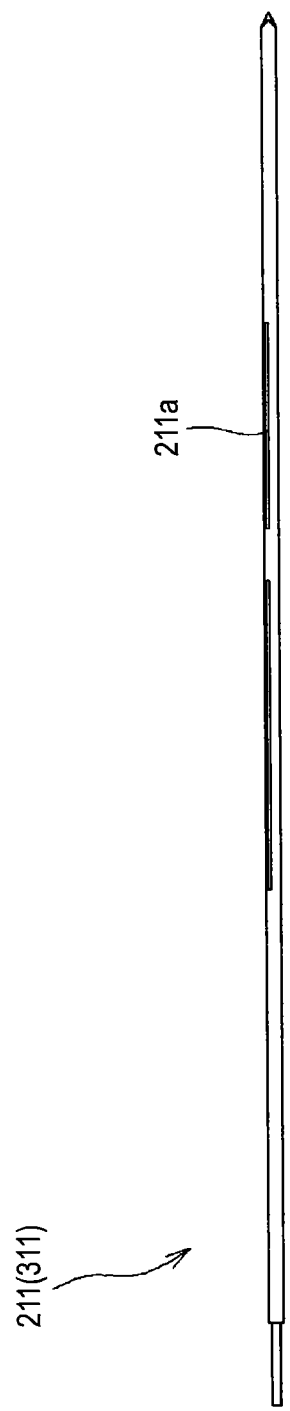
FIG. 12 is a front view showing the appearance of the piercer.

FIG. 4 is a view showing the vicinity of the piercer 211 (311). As shown in FIG. 4, the blood sample processing apparatus 1 includes the piercer 211 (311) as a specimen aspiration tube and a piercer moving section 212 (312) as a penetration driver which causes the piercer 211 (311) to penetrate the lid of a specimen container 101. The piercer 211 (311) is formed such that the front end thereof can penetrate a sealing lid 102 (see FIGS. 7 to 9) (to be described later) of a specimen container 101. Moreover, as shown in FIG. 12, in the outer circumferential surface of the piercer 211 (311), a groove 211a extending in a longitudinal direction of the piercer 211 (311) is formed, and when the piercer 211 (311) penetrates the lid of the specimen container 101, the inside of the specimen container 101 is opened to the air via the above-described groove 211a. The piercer moving section 212 (312) has a function of moving the piercer 211 (311) in a vertical direction (in a direction of the arrows Z1 and Z2). The piercer moving section 212 (312) has a horizontal arm 213 (313) which fixes and holds the piercer 211 (311), a threaded shaft 214 (314) which penetrates the horizontal arm 213 (313) in the vertical direction (in the direction of the arrows Z1 and Z2), and a nut 215 (315) which is threadably mounted on the threaded shaft 214 (314). Further, the piercer moving section 212 (312) has a slide rail 216 (316) which is disposed parallel to the threaded shaft 214 (314) (in the direction of the arrows Z1 and Z2), a sliding member 217 (317) which is slidably mounted on the slide rail 216 (316) and a stepping motor 218 (318). The horizontal arm 213 (313) is fixed to the nut 215 (315) and the sliding member 217 (317).

The detecting section 23 (33) is configured to perform RBC detection (detection of red blood cells) and PLT detection (detection of platelets) by a sheath flow DC detection method and perform HGB detection (detection of hemoglobin in blood) by a SLS-hemoglobin method. In addition, the detecting section 23 (33) is also configured to perform WBC detection (detection of white blood cells) by a flow cytometry method using a semiconductor laser.

The detection result obtained by the detecting section 23 (33) is transmitted as measurement data (measurement result) of the specimen to the control apparatus 5. This measurement data becomes a base for the final analysis result (the number of red blood cells, the number of platelets, the amount of hemoglobin, the number of white blood cells and the like) which is provided to a user.

Figure 5:
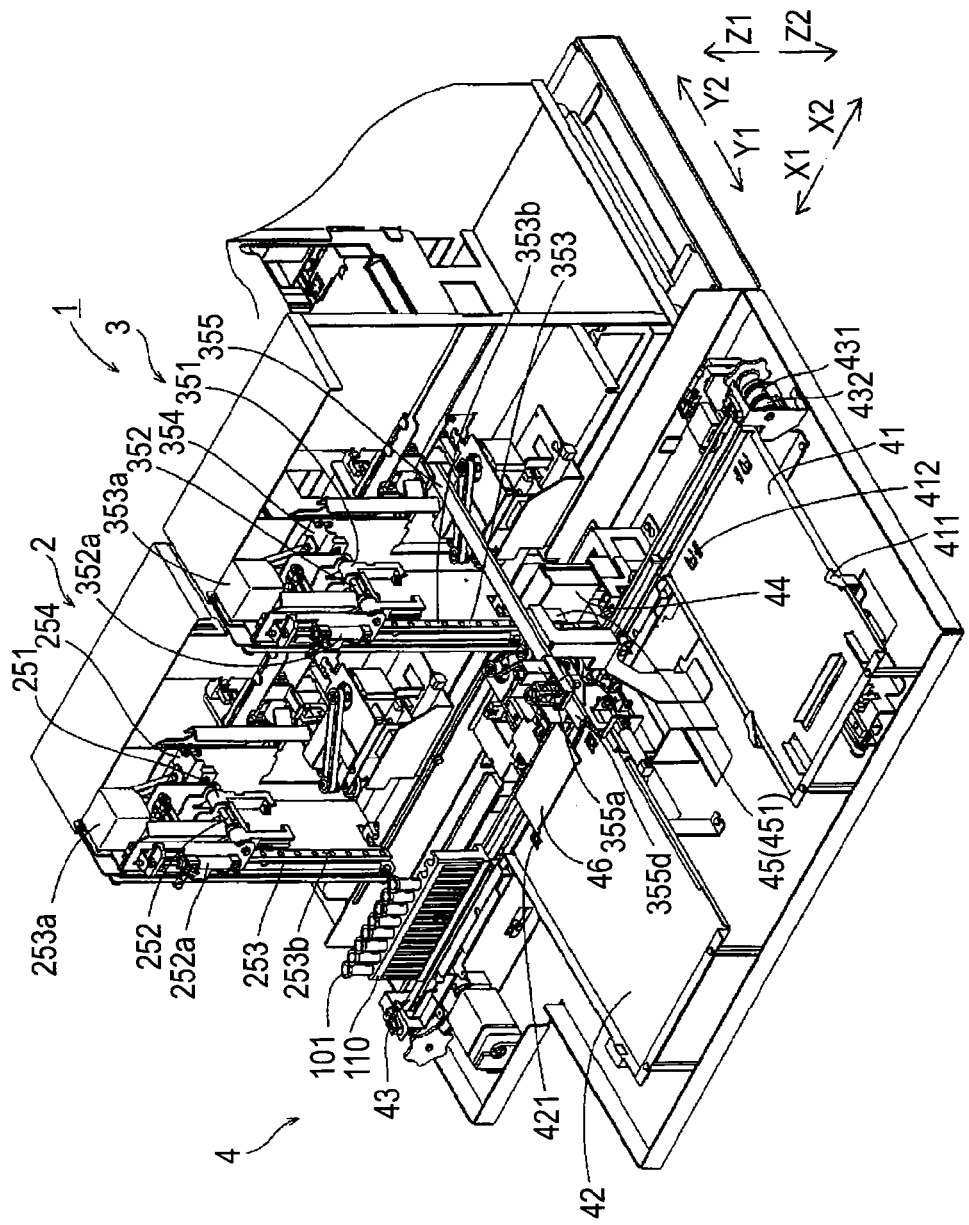
FIG. 5 is a perspective view showing the measuring units and the specimen transport apparatus of the blood sample processing apparatus shown in FIG. 1.

As shown in FIG. 5, the specimen container transport section 25 (35) (see FIG. 3) has a hand section 251 (351) which is a container holder capable of holding a specimen container 101, an opening-closing section 252 (352) which opens and closes the hand section 251 (351), a vertical moving section 253 (353) which linearly moves the hand section 251 (351) in the vertical direction (in the direction of the arrows Z1 and Z2) and a stirring motor section 254 (354) which is a rotation driver for moving (rotating) the hand section 251 (351) like a pendulum between its upright state and inclining state. The stirring motor section 254 (354) is configured to move (rotate) the hand section 251 (351) like a pendulum between its upright state and inclining state by the power generated by the stepping motor. Further, as shown in FIG. 3, the specimen container transport section 25 (35) has a specimen container transfer section 255 (355) which substantially horizontally moves a specimen container 101 in the direction of the arrows Y1 and Y2 and a bar-code reading section 256 (356).

The hand section 251 (351) is disposed above the transport path of a rack 110 transported by the specimen transport apparatus 4. In addition, the hand section 251 (351) is configured to be moved downward (in the direction of the arrow Z2) when a specimen container 101 is transported to a first ejection position 43a and a second ejection position 43b (see FIG. 3) by the specimen transport apparatus 4 and to be then opened and closed by the opening-closing section 252 (352), thereby gripping the specimen container 101 stored in a rack 110.

In addition, the hand section 251 (351) is configured to move the gripped specimen container 101 upward (in the direction of the arrow Z1) to eject the specimen container 101 from the rack 110, and then is moved like a pendulum by the stirring motor section 254 (354) (for example, reciprocated 10 times). In this manner, the hand section 251 (351) can stir the blood in the gripped specimen container 101. After the stirring, the hand section 251 (351) is configured to open the gripping of the specimen container 101 by the opening-closing section 252 (352) after moving downward (in the direction of the arrow Z2). In greater detail, the hand section 251 (351) is configured to set the specimen container 101 in a first specimen setting section 255a (355a) which is moved to a specimen setting position 610 (710) (see FIG. 3) by the specimen container transfer section 255 (355). In addition, as shown in FIG. 3, when viewed from the top, the first ejection position (specimen container ejection position) 43a and the specimen setting position (specimen container setting position) 610 are disposed so as to overlap with each other, and the second ejection position (specimen container ejection position) 43b and the specimen setting position (specimen container setting position) 710 are disposed so as to overlap with each other.

The opening-closing section 252 (352) is configured to open and close the hand section 251 (351) in order to grip a specimen container 101 using the power generated by an air cylinder 252a (352a).

The vertical moving section 253 (353) is configured to move the hand section 251 (351) in the vertical direction (in the direction of the arrows Z1 and Z2) along a rail 253b (353b) using the power generated by the stepping motor 253a (353a).

The chuck section 27 (37) is configured to fix and hold a specimen container 101 which is transferred to the aspiration position 600 (700).

A before-analysis rack holder 41 has a rack input section 411 and is configured to push out racks 110 held in the before-analysis rack holder 41 one by one onto a rack transport section 43 by moving the rack input section 411 in the direction of the arrow Y2. The rack input section 411 is configured to be driven by a stepping motor (not shown) which is provided below the before-analysis rack holder 41. In addition, the before-analysis rack holder 41 has a regulating section 412 (see FIG. 5) in the vicinity of the rack transport section 43 and is configured to regulate the movement of a rack 110 in order not to return the rack 110, which is pushed out onto the rack transport section 43 once, to the inside of the before-analysis rack holder 41.

An after-analysis rack holder 42 has a regulating section 421 (see FIG. 4) in the vicinity of the rack transport section 43 and is configured to regulate the movement of a rack 110 in order not to return the rack 110, which is moved to the inside of the after-analysis rack holder 42 once, to the rack transport section 43.

As shown in FIG. 3, the rack transport section 43 is configured to transport a rack 110 in order to transfer a specimen container 101 held in the rack 110 to the first ejection position 43a for providing the specimen to the first measuring unit 2 and to the second ejection position 43b for providing the specimen to the second measuring unit 3. Further, the rack transport section 43 is configured to transport a rack 110 in order to transfer a specimen container 101 up to a specimen existence confirmation position 43c for confirming the existence of the specimen container 101 storing the specimen by an existence detection sensor 45 and a reading position 43*d* for reading the bar-code of the specimen container 101 storing the specimen by a bar-code reading section 44.

In addition, as shown in FIG. 5, the rack transport section 43 has two belts, that is, a first belt 431 and a second belt 432 which can be moved independently of each other.

The existence detection sensor 45 is a contact sensor having a contact piece shaped like a short split curtain (see FIG. 5) 451, a light-emitting element (not shown) emitting light and a light-receiving element (not shown). The existence detection sensor 45 is configured such that the contact piece 451 is bent by being brought into contact with a detection target material to be detected, and as a result, the light emitted from the light-emitting element is reflected by the contact piece 451 and enters the light-receiving element. In this manner, when a specimen container 101 as a detection target which is stored in a rack 110 passes under the existence detection sensor 45, the contact piece 451 is bent by the specimen container 101 and the existence of the specimen container 101 can thus be detected.

A rack output section 46 is disposed so as to be opposed to the after-analysis rack holder 42 with the rack transport section 43 interposed therebetween, and is configured to be horizontally moved in the direction of the arrow Y1. In this manner, when a rack 110 is transported between the after-analysis rack holder 42 and the rack output section 46, the rack output section 46 is moved to the after-analysis rack holder 42 side to press and move the rack 110 to the inside of the after-analysis rack holder 42.

As shown in FIGS. 1 to 3 and 6, the control apparatus 5 is composed of a personal computer (PC) or the like and includes a controller 51 (see FIG. 6) having a CPU, a ROM, a RAM and the like, a display section 52 and an input device 53. In addition, the display section 52 is provided in order to display the analysis result obtained by analyzing data of digital signals transmitted from the first measuring unit 2 and the second measuring unit 3.

Figure 6:
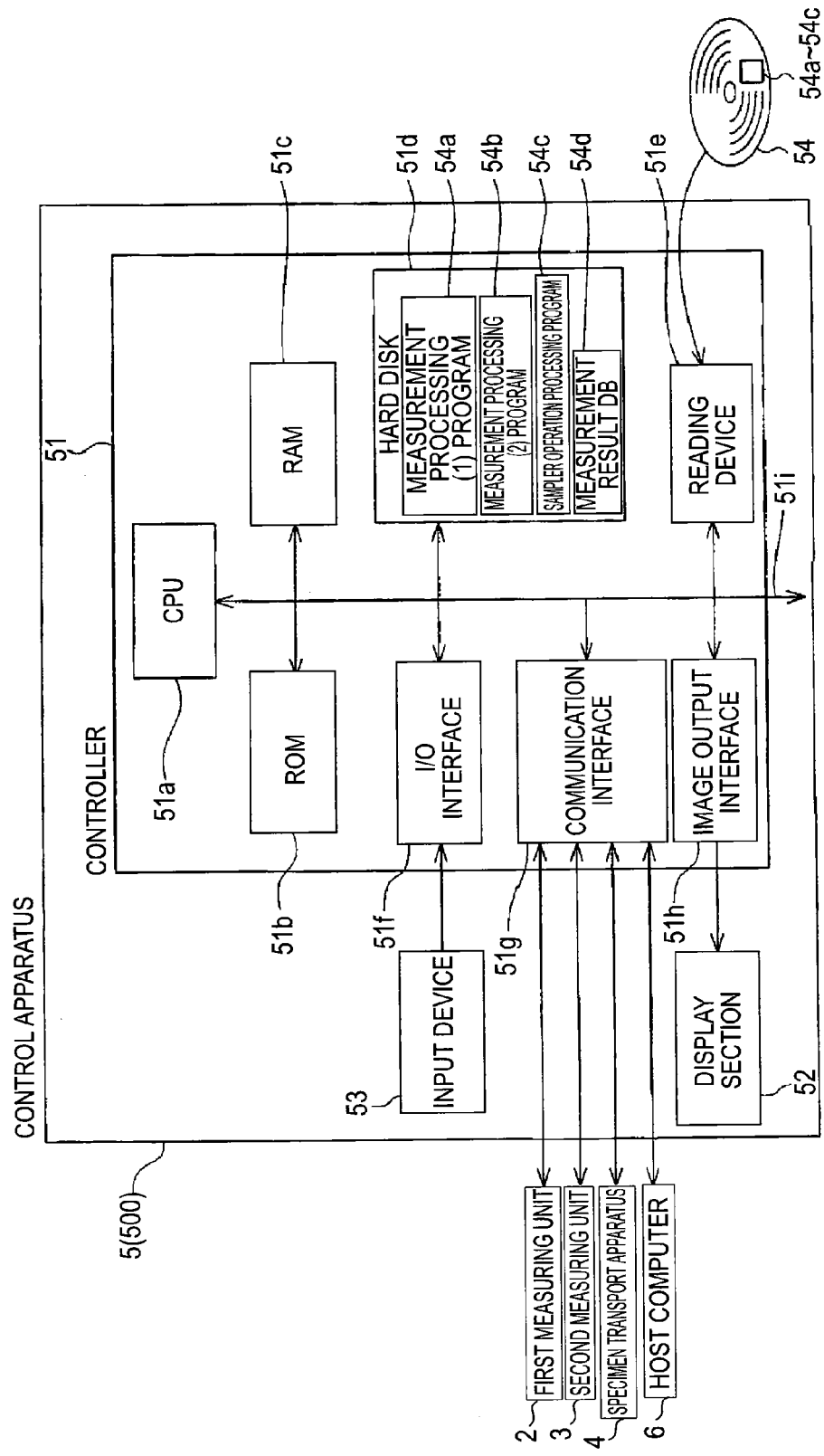
FIG. 6 is a block diagram for explaining a control apparatus of the blood sample processing apparatus shown in FIG. 1.

In addition, as shown in FIG. 6, the control apparatus 5 is composed of a computer 500 mainly including the controller 51, the display section 52 and the input device 53. The controller 51 mainly includes a CPU 51*a*, a ROM 51*b*, a RAM 51*c*, a hard disk 51*d*, a reading device 51*e*, an I/O interface 51*f*, a communication interface 51*g* and an image output interface 51*h*. The CPU 51*a*, ROM 51*b*, RAM 51*c*, hard disk 51*d*, reading device 51*e*, I/O interface 51*f*, communication interface 51*g* and image output interface 51*h* are connected by a bus 51*i*.

The CPU 51*a* can execute computer programs stored in the ROM 51*b* and computer programs loaded to the RAM 51*c*. When the CPU 51*a* executes application programs 54*a*, 54*b* and 54*c* to be described later, the computer 500 functions as the control apparatus 5.

The ROM 51*b* is composed of a mask ROM, a PROM, an EPROM, an EEPROM or the like, and computer programs which are executed by the CPU 51*a* and data which are used in the execution of the programs are recorded therein.

The RAM 51*c* is composed of a SRAM, a DRAM or the like. The RAM 51*c* is used to read computer programs which are recorded in the ROM 51*b* and the hard disk 51*d*. In addition, the RAM is used as a work area of the CPU 51*a* when these computer programs are executed.

In the hard disk 51*d*, various computer programs for execution by the CPU 51*a*, such as an operating system and an application program, and data which are used to execute the computer programs, are installed. A measurement process (1) program 54*a* for the first measuring unit 2, a measurement process (2) program 54*b* for the second measuring unit 3 and a sampler operation processing program 54*c* for the specimen transport apparatus 4 are also installed in this hard disk 51*d*. By executing these application programs 54*a* to 54*c* with the CPU 51*a*, the operations of sections in the first measuring unit 2, second measuring unit 3 and specimen transport apparatus 4 are controlled. A measurement result database 54*d* is also installed in the hard disk 51*d*.

The reading device 51*e* is composed of a flexible disk drive, a CD-ROM drive, a DVD-ROM drive or the like and can read computer programs or data which are recorded in a portable recording medium 54. In addition, the application programs 54*a* to 54*c* are stored in the portable recording medium 54 and the computer 500 can read the application programs 54*a* to 54*c* from the portable recording medium 54 and install the application programs 54*a* to 54*c* in the hard disk 51*d*.

The above-described application programs 54*a* to 54*c* are provided by the portable recording medium 54 and can be also provided from an external device, which is connected to the computer 500 by an electric communication line (which may be wired or wireless) to communicate therewith, through the electric communication line. For example, the application programs 54*a* to 54*c* are stored in the hard disk of a server computer on the internet and the computer 500 accesses the server computer to download the application programs 54*a* to 54*c* and to install the programs in the hard disk 51*d*.

Further, in the hard disk 51*d*, for example, an operating system for providing a graphical user interface environment, such as Windows (registered trade name) which is made and distributed by Microsoft Corporation in America, is installed. In the following description, the application programs 54*a* to 54*c* operate on the above-described operating system.

The I/O interface 51*f* is composed of, for example, a serial interface such as USB, IEEE1394 or RS-232C, a parallel interface such as SCSI, IDE or IEEE1284, and an analog interface including a D/A converter and an A/D converter. The input device 53 is connected to the I/O interface 51*f* and a user uses the input device 53 so as to input data to the computer 500.

For example, the communication interface 51*g* is an Ethernet (registered trade name) interface. By the communication interface 51*g*, the computer 500 can transmit and receive data to and from the first measuring unit 2, second measuring unit 3, specimen transport apparatus 4 and host computer 6 by using a predetermined communication protocol.

The image output interface 51*h* is connected to the display section 52 composed of an LCD or a CRT so as to output to the display section 52 a picture signal corresponding to image data provided from the CPU 51*a*. The display section 52 is configured to display an image (screen) in accordance with an input picture signal.

Due to the above-described configuration, the controller 51 is configured to analyze the components of an analysis target by using the measurement result transmitted from the first measuring unit 2 and the second measuring unit 3 and to obtain the analysis result (the number of red blood cells, the number of platelets, the amount of hemoglobin, the number of white blood cells and the like).

[Blood Sample Processing Method]

Figure 13:
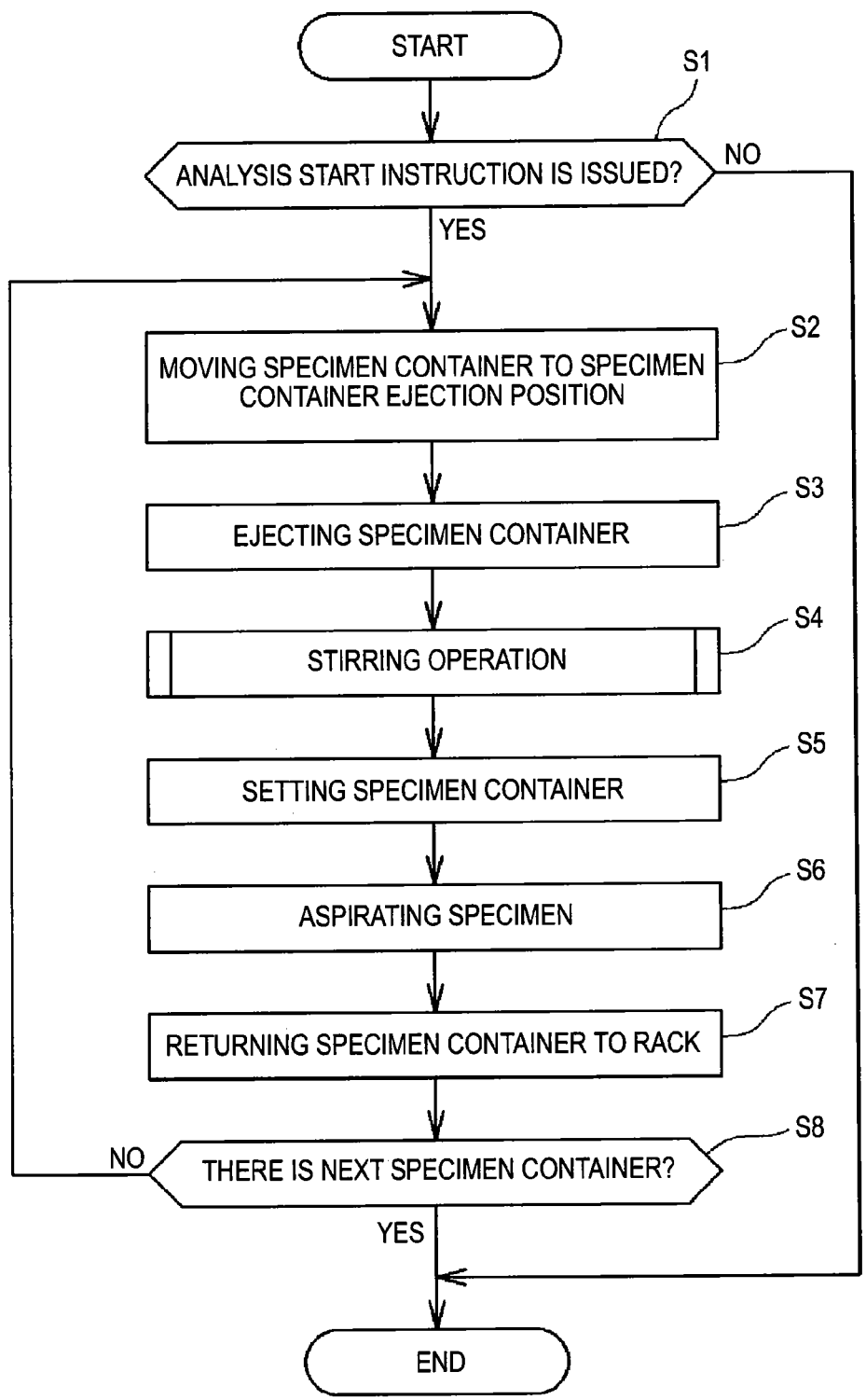
FIG. 13 is a flowchart showing the processing flow of a blood sample processing method according to the present embodiment.
Figure 14:
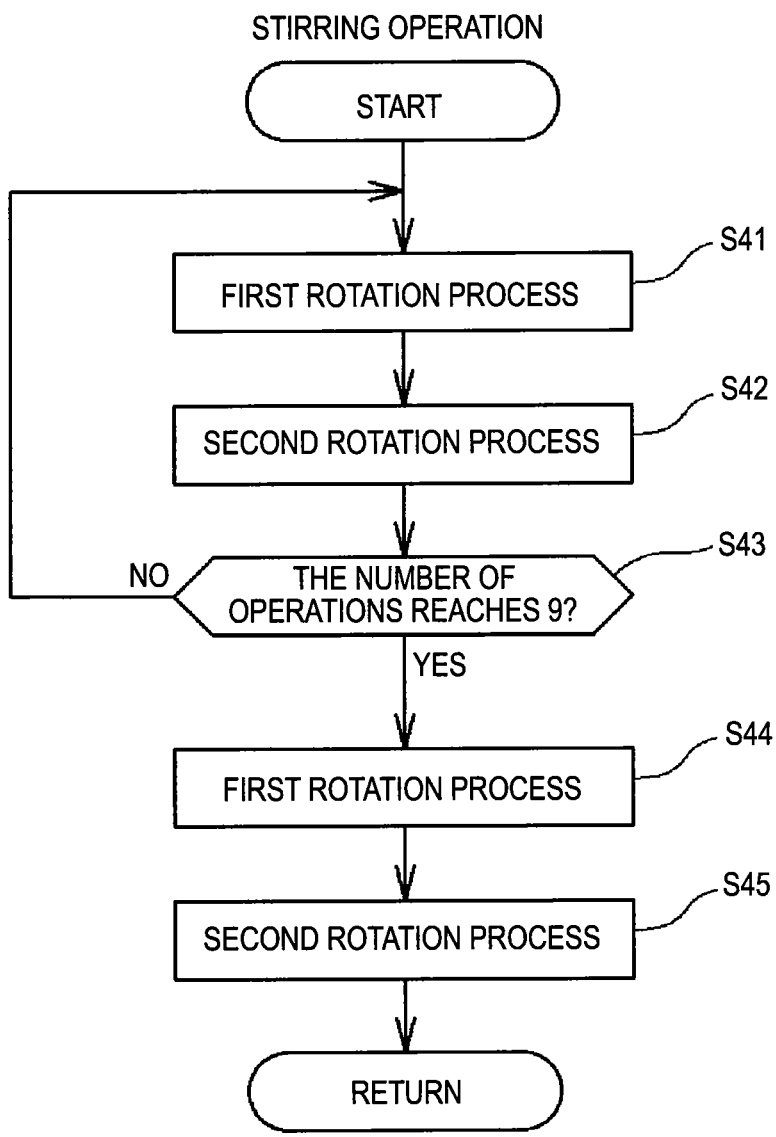
FIG. 14 is a flowchart showing the flow of a stirring operation according to the present embodiment.

Next, an embodiment of a blood sample processing method of the present invention, which uses the above-described blood sample processing apparatus 1, will be described focusing on a characteristic inclining-stirring operation by using FIGS. 13 and 14. Since the first measuring unit 2 and the second measuring unit 3 perform the analysis including stirring and aspiration of a specimen with the same operation, a blood sample processing method of the first measuring unit 2 will be described hereinafter and a blood sample processing method of the second measuring unit 3 will be omitted.

First, a user sets a rack 110, in which a specimen container 101 with a lid storing a blood sample as an analysis target is installed, on the specimen transport apparatus 4. Next, when determining that an analysis start instruction is issued by the pressing of the start button (Step S1), the CPU 51*a* of the control apparatus 5 controls the transport of the rack 110 by the specimen transport apparatus 4 to position the above-described specimen container 101 at the first ejection position (specimen container ejection position) 43*a* (Step S2).

The CPU 51*a* ejects the specimen container 101 from the rack 110 by using the hand section 251 (Step S3). In greater detail, the CPU 51*a* drives the vertical moving section 253 such that the hand section 251 in an opened state moves down from the upper side and is stopped at a specimen container holding position where the specimen container 101 can be held.

Next, the CPU 51*a* drives the opening-closing section 252 to close the hand section 251 and thus the specimen container 101 is held. In addition, the CPU 51*a* drives the vertical moving section 253 again such that the hand section 251 is lifted in a state of holding the specimen container 101, and the specimen container 101 is ejected from the rack 110 and stopped at a predetermined position. In this state, the specimen container 101 is in an upright state such that the axis thereof in a longitudinal direction is substantially in the vertical direction.

<Stirring Process>

Figure 10:
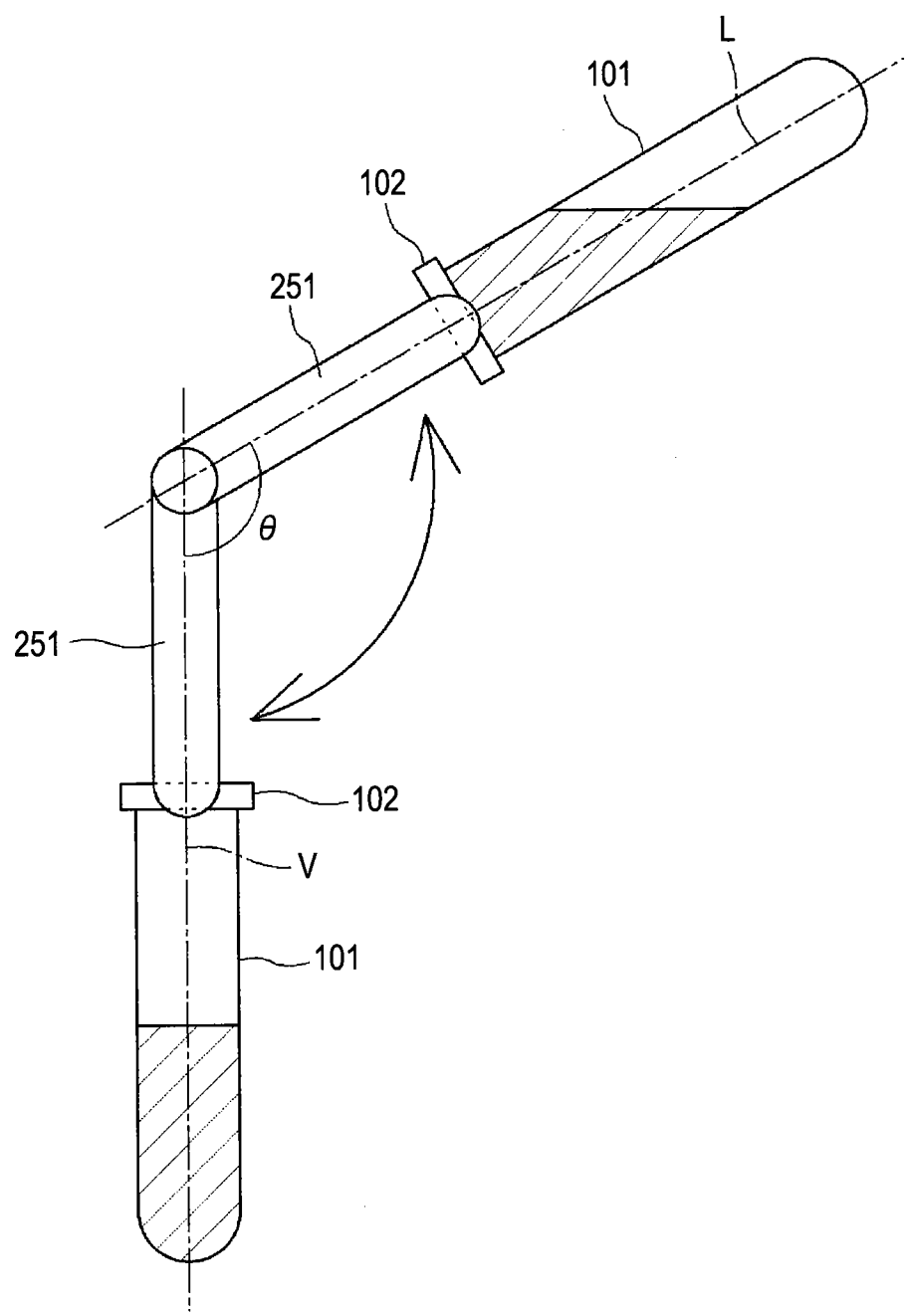
FIG. 10 is a diagram explaining an example of an inclining-stirring operation of the present invention.

Next, the CPU 51*a* performs an inclining-stirring operation of the specimen container 101 by driving the stirring motor section 254 (step S4). The flow of this stirring operation will be described later by using FIG. 14. In this stirring process, the hand section 251 holding the specimen container 101 rotates forward and backward to stir the blood sample stored in the specimen container 101. FIG. 10 is a diagram showing the inclining-stirring operation of the specimen container 101 by the hand section 251, and shows both of an aspect in which the specimen container 101 is held in an upright state by the hand section 251 and an aspect in which the specimen container 101 is held in an inclining state by the hand section 251. As shown in FIG. 10, the hand section 251 performs the inclining-stirring operation which includes a first rotation process of rotating the hand section to reach an inclining state in which the bottom portion of the specimen container 101 is positioned higher than the sealing lid 102 of the specimen container 101 and a second rotation process of inversely rotating the hand section to return the specimen container 101 to an upright state from the inclining state.

In the above-described inclining state, an angle θ which is formed between a vertical line V and an axis L in the longitudinal direction of the specimen container 101 is about 127 degrees (see FIG. 10).

The hand section 251 repeatedly performs an inclining-stirring operation, in which the first rotation process and the second rotation process are set as one cycle, ten times. In addition, the second rotation process at the final cycle is carried out for 0.8 seconds or longer (in this embodiment, about 1.87 seconds). In this embodiment, the first rotation processes and the second rotation processes other than the second rotation process at the final cycle are performed for a shorter time than the second rotation process at the final cycle, for example, for about 0.4 to 0.6 seconds (in this embodiment, about 0.43 seconds). In this manner, by performing the second rotation processes other than the second rotation process at the final cycle for a shorter time than the second rotation process at the final cycle, the time required for all of the multiple inclining-stirring operations can be reduced.

Due to the above-described inclining-stirring operations, the blood sample adheres to the back side of the sealing lid 102 of the specimen container 101. However, by slowly performing the dropping process at the final cycle for 0.8 seconds or longer, the blood sample adhering to the back side of the sealing lid 102 of the specimen container 101 can be moved to the bottom portion of the container. The principle whereby the blood sample adhered to the back side of the sealing lid 102 runs down into the container can be assumed and confirmed as follows.

Figure 7:
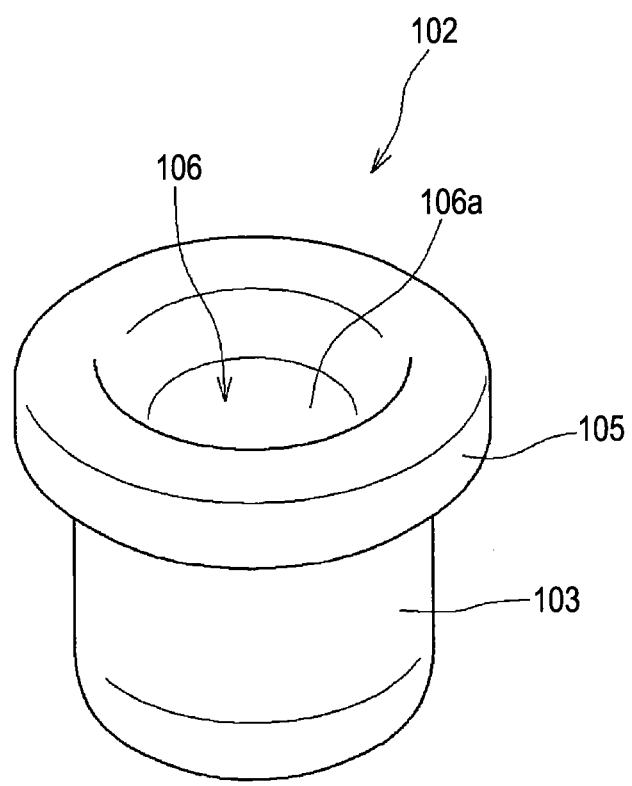
FIG. 7 is a perspective view of an example of a lid which is used in a specimen container, viewed from the upper side.
Figure 8:
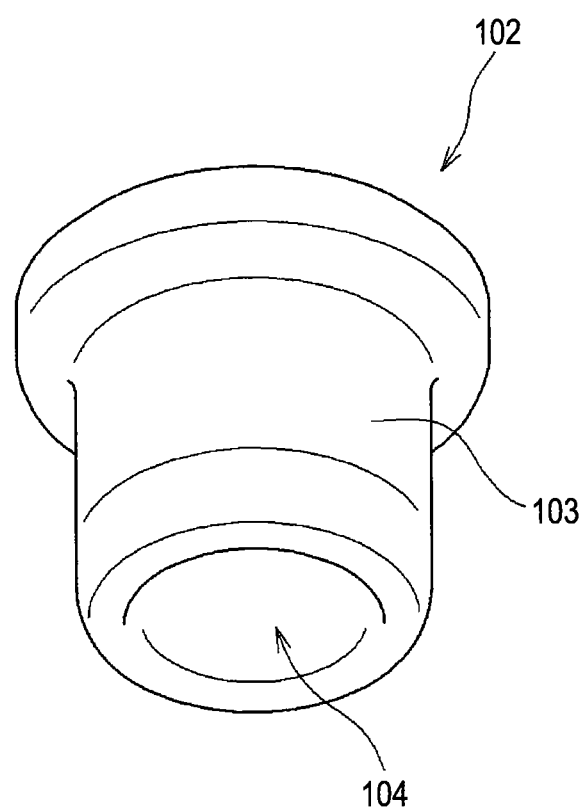
FIG. 8 is a perspective view of the lid shown in FIG. 7, viewed from the lower side.
Figure 9:
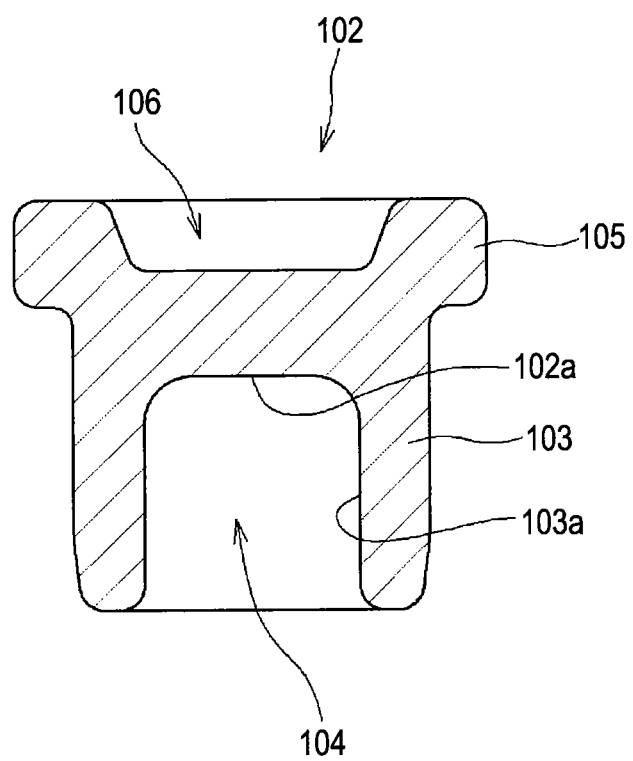
FIG. 9 is a longitudinal sectional view of the lid shown in FIG. 7.

FIG. 7 is a perspective view of the sealing lid 102 viewed from the upper side, FIG. 8 is a perspective view of the same sealing lid viewed from the lower side, and FIG. 9 is a longitudinal sectional view of the sealing lid 102 shown in FIGS. 7 and 8. The sealing lid 102 is made of a synthetic resin such as silicon rubber having elasticity and has a lid main body 103 which is inserted into the opening of a specimen container 101. In the lower surface of the lid main body 103, a concave portion or recess 104 is formed and a brim section 105 is formed at the upper end portion of the circumferential surface of the lid main body 103. A concave portion or recess 106 is also formed in the upper surface of the lid main body 103 and a piercer 211 pierces a bottom surface 106*a* of the concave portion 106.

Figure 11C:
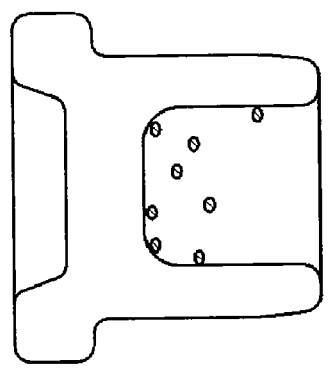
FIGS. 11A-11C are diagrams showing transitions in which blood adhering to the back side of the lid flows to a bottom portion.
Figure 11B:
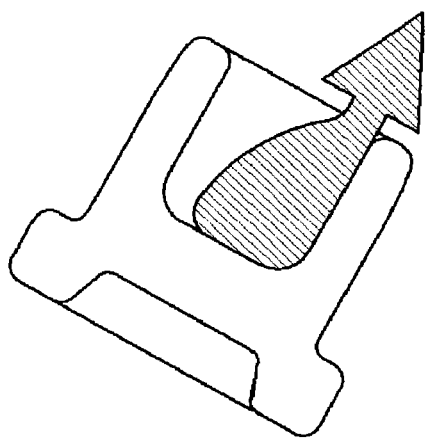
Figure 11A:
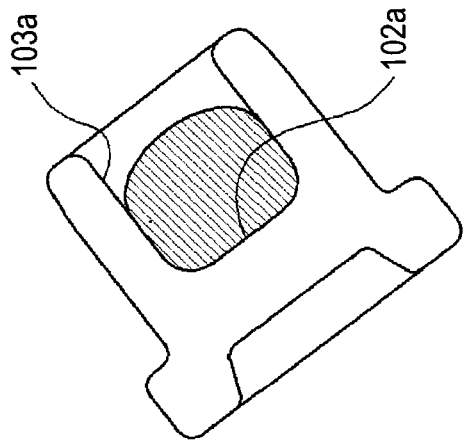

When the inclining-stirring operation is applied to the specimen container 101 sealed by the sealing lid 102 having the above-described configuration, the blood sample moving to the inside of the concave portion 104 of the sealing lid 102 in an inclining state adheres to a back surface 102*a* of the sealing lid 102 and an inner circumferential surface 103*a* of the lid main body 103 in a spherical shape by the action of surface tension on the interface of the blood sample (see FIG. 11A).

When the specimen container 101 is slowly returned to the upright state from the inclining state for 0.8 seconds or longer, as shown in FIG. 11B, a time at which the specimen container 101 is tilted in a state in which the sealing lid 102 is positioned higher than the bottom portion of the specimen container 101 is increased. When the specimen container 101 is tilted in a state in which the sealing lid 102 is positioned higher than the bottom portion of the specimen container 101, the surface area of the blood sample is increased, the spherical shape collapses, and as a result, surface tension is decreased. That is, the pressure in the blood sample is decreased and a force pulling the molecules of the surface of the blood sample to the inside is decreased. In this manner, it is thought that a force causing the blood sample to remain on the back side of the sealing lid 102 is decreased, the blood sample runs down to the bottom portion of the specimen container 101 due to the influence of gravity, and as a result, the amount of blood sample adhering to and remaining on the back side of the sealing lid 102 can be significantly decreased (see FIG. 11C).

Table 1 shows results which are obtained by surveying a blood leakage state (whether or not the blood is leaked from the groove in the longitudinal direction formed in the outer circumferential surface of the piercer when the piercer penetrates the lid after stirring) when a time required for the second rotation process at the final cycle is variously changed in the case in which a 10-cycle inclining-stirring operation is performed. As the sealing lid, a lid of the type shown in FIGS. 7 to 9 is used and the amount of blood stored in the specimen container is 4 ml.

The inclining-stirring operation is performed by using a pulse motor and set pulse values in the second rotation process at the final cycle are set as a low-speed value and a high-speed value shown in Table 1. In greater detail, the "set pulse value" is the number of driving pulses (pulse speed) which are applied to the pulse motor per second. In this inclining-stirring operation, the pulse motor is driven such that the pulse speed increases from the set pulse value shown by a low-speed value to the set pulse value shown by a high-speed value, and after the elapse of a predetermined time, the pulse motor is driven such that the pulse speed decreases from the set pulse value shown by a high-speed value to the set pulse value shown by a low-speed value. Accordingly, the hand section is set so as to rotate at a low speed for a predetermined time after the start of the rotation and a predetermined time before the end of the rotation and to rotate at a high speed for the remaining time. In other words, when the horizontal axis represents time and the vertical axis represents pulse speed, the pulse value is changed such that the pulse speed changes in a trapezoidal shape. The "processing time" in Table 1 is a time required for the second rotation process at the final cycle, and in the test shown in Table 1, the second rotation processes other than the second rotation process at the final cycle and the first rotation processes are performed for 0.43 seconds, respectively.

or longer and it was found that the amount of blood sample adhering to and remaining on the back side of the lid can be more significantly decreased by setting the above-described time to 1.4 seconds or longer.

Next, the flow of the inclining-stirring operation of the specimen container 101 will be described by using FIG. 14. In the following description, a rotation process of shifting a specimen container 101 in an upright state into an inclining state is referred to as "first rotation process" and a rotation process of returning a specimen container 101 in an inclining state to an upright state is referred to as "second rotation process", and particularly, the second rotation process which returns a specimen container 101 in an inclining state to an upright state in the final cycle is referred to as "second low-speed rotation process".

First, the CPU 51*a* performs the first rotation process of rotating a specimen container 101 from an upright state to an inclining state (Step S41), and then performs the second rotation process of returning the specimen container 101 to an upright state from an inclining state (Step S42). The respective first and second rotation processes are performed for 0.43 seconds. Next, the CPU 51*a* determines whether or not the number of inclining-stirring operations in which the first rotation process and the second rotation process are set as one cycle reaches 9 (Step S43), and when the number of inclining-stirring operations does not reach 9, the CPU 51*a* repeatedly performs the operations of Steps S41 and S42.

When the number of the inclining-stirring operations reaches 9, the CPU 51*a* performs the first rotation process once again (Step S44), and then performs the second low-speed rotation process (Step S45). Then, the process returns to the blood sample processing. In the second low-speed

TABLE 1

| No. | Stirring Condition | Returning Operation of Final Stirring Set Pulse Value | | The Number of Specimen Containers Without Leakage (Amount of Blood 4 mL) | | Processing Time [s] |
| --- | --- | --- | --- | --- | --- | --- |
| | | [Low Speed] | [High Speed] | Among 10 Containers | Among 100 Containers | |
| 1 | Ten-time Stirring | 100 | 600 | 0 | — | 0.43 |
| 2 | * Returning | 100 | 300 | 9 | — | 0.72 |
| 3 | Operation of Final | 100 | 200 | 10 | — | 0.94 |
| 4 | Stirring is Slowly | 75 | 150 | 10 | 90 | 1.25 |
| 5 | Performed | 60 | 120 | 10 | 99 | 1.56 |
| 6 | | 50 | 100 | 10 | 100 | 1.87 |

As can be seen from Table 1, when all the second rotation processes and the first rotation processes in the 10-cycle inclining-stirring operation are performed for 0.43 seconds, respectively (Test No. 1), leakage of the blood is observed in all of the ten specimen containers. However, when the second rotation process at the final cycle is performed for 0.94 seconds, which is longer than 0.8 seconds (Test No. 3), leakage of the blood is not observed in any of the ten specimen containers. In addition, when the second rotation process at the final cycle is performed for 1.56 seconds, which is longer than 1.4 seconds (Test No. 5), leakage of the blood is not observed in any of the ten specimen containers, and even when the number of specimen containers is increased to 100, leakage of the blood is observed in only one specimen container.

Accordingly, it was found that the amount of blood sample adhering to and remaining on the back side of the lid can be significantly decreased by setting a time required for the second rotation process at the final cycle to 0.8 seconds rotation process in Step S45, an operation of returning the specimen container 101 in an inclining state to an upright state is performed for a longer time than other processes, that is, 1.87 seconds.

During the stirring operation of the specimen container 101, the rack 110 is evacuated from the specimen container ejection position 43*a* and the specimen setting section 255*a* moves forward up to a predetermined position positioned below the hand section 251 due to the driving of the specimen container transport section 255. After the stirring, the CPU 51*a* moves the hand section 251 down and opens the hand section 251, and thus the specimen container 101 held in the hand section 251 is set in the specimen setting section 255*a* (Step S5).

Next, the hand section 251 is lifted, and the specimen setting section 255*a* is drawn into the apparatus by the driving of the specimen container transport section 255 and positioned at a predetermined position.

<Aspiration Process>

Next, the CPU 51a performs an operation of aspirating the specimen from the specimen container 101 (Step S6). In greater detail, in a state in which the specimen container 101 is held by the chuck section 27 so as not to move due to the control of the CPU 51a, the piercer 211 is driven by the piercer moving section 212 and moves down from the upper side to penetrate the sealing lid 102 of the specimen container 101, and is stopped at a predetermined position. In this penetration operation, as described above, the blood sample adhering to the back side of the lid 102 moves to the bottom portion of the container during the inclining-stirring operation and thus does not remain on the back side of the lid 102. Accordingly, there is no leakage to the outside from the groove 211a in the outer circumferential surface of the piercer 211 for opening to the atmosphere.

After the piercer 211 is stopped at the predetermined position in the specimen container 101, a predetermined amount of the blood sample is aspirated by the piercer 211. After the aspiration, the piercer 211 is lifted and the aspirated blood sample is mixed with a reagent in a reaction container of the sample preparation section 22, and thus a sample for measurement is prepared. Then, the prepared sample for measurement is transferred to the detecting section 23 and predetermined items are detected (measured) in the detecting section 23. The detection result is transmitted to the controller 51 and the components of the analysis target are analyzed in the controller 51. The obtained analysis result is displayed on the display section 52.

After the piercer 211 is lifted, the CPU 51a performs an operation for returning the specimen container 101 to the original rack 110 (Step S7). In greater detail, due to the control of the CPU 51a, the specimen setting section 255a is moved forward once again by the driving of the specimen container transport section 255 and is stopped at the specimen container setting position. Next, the hand section 251 moves down from the upper side and is stopped at the specimen container holding position.

Next, the hand section 251 is closed to hold the specimen container 101 of the specimen setting section 255a, and after that, the hand section 251 is lifted and stopped at a predetermined position. During the lifting of the hand section 251 holding the specimen container 101, the specimen setting section 255a is drawn into the apparatus by the driving of the specimen container transport section 255. In addition, the evacuated rack 110 advances and is stopped at a predetermined position.

Next, the hand section 251 moves down and inserts the specimen container 101 into the rack 110. Then, the hand section 251 is opened by the opening driving of the opening-closing section 252 and thus the specimen container 101 is set in the rack 110. Then, the hand section 251 is lifted. After that, the CPU 51a determines whether or not there is a specimen container storing a blood sample to be analyzed next (Step S8). When there is a next specimen container, the process proceeds to Step S2 and the rack 110 is moved to position a specimen container 101 storing a blood sample to be analyzed next at the specimen container ejection position. The above-described sequence of operations starting from the dropping of the opened hand section 251 is repeatedly performed in the same manner. In Step S8, when it is determined that there are no specimen containers storing a blood sample to be analyzed next, the CPU 51a completes the process.

As described above, in this embodiment, since the inclining-stirring operation of a specimen container is repeatedly performed and the second rotation process of the final inclining-stirring operation is performed for a longer time (0.8 seconds or longer) than in other second rotation processes, the blood sample adhering to the back side of the lid of the specimen container can be moved to the bottom portion of the specimen container. Accordingly, at the time point when the inclining-stirring operation is completed, a state in which the blood sample adheres to the back side of the lid of the specimen container can be resolved or suppressed. For example, the leakage of the blood sample in the specimen container out of the container when a piercer penetrates the lid can be resolved or suppressed.

In addition, since a state in which the blood sample adheres to the back side of the lid of the specimen container can be resolved or suppressed, wastage of a portion of the blood sample collected from a patient can be suppressed.

In the above-described blood sample processing method, the second rotation process which is performed just before the piercing of the piercer is slowly carried out for 0.8 seconds or longer and the time required for other second rotation processes and first rotation processes is not particularly limited. However, from the point of view of decreasing the total processing time, it is preferable that other second rotation processes and first rotation processes are performed for a shorter time than the second rotation process which is performed just before the piercing of the piercer.

In the above-described embodiments, the inclining-stirring operation is an operation reciprocating from an upright state to an inclining state with an angle of about 127 degrees between the vertical line and the axis of the specimen container. However, as long as the inclining state exists in which the bottom portion of the specimen container is positioned higher than or as high as the lid, the inclining-stirring operation is not limited to the exemplified operation and various inclining-stirring operations can be performed. For example, the above-described angle θ may be smaller than or larger than 127 degrees. For example, the angle θ may be 180 degrees or may be 90 degrees. In addition, the hand section 251 may not only be rotated in a space in one direction viewed from the vertical line V as in this embodiment, but may also be rotated in a space in another direction viewed from the vertical line V in addition to the above-described space.

In the above-described embodiments, a specimen container 101 in an upright state is rotated in one direction to be shifted into an inclining state, and then the specimen container 101 is inversely rotated to return to the original upright state. However, the present invention is not limited thereto. For example, the specimen container 101 in an upright state may be rotated in one direction to be shifted into an inclining state and may be further rotated in the one direction to return to the original upright state from the inclining state.

In the above-described embodiments, a specimen container 101 is stirred by repeating an operation in which the specimen container 101 in an upright state is shifted into an inclining state and is stopped once and then the specimen container 101 is returned to the original upright state. However, the present invention is not limited thereto. For example, an operation may be continuously repeated in which the specimen container 101 in an upright state is rotated to be shifted into an inclining state and then is rotated by 360 degrees as it is without stopping the specimen container 101 so as to be returned to the original upright state. In the case of this stirring operation, a process of returning the specimen container in an inclining state to an upright state at the final cycle is performed at a lower speed than other processes, and thus the amount of blood sample adhering to and remaining on the back side of the lid of the specimen container 101 can be decreased.

In the above-described embodiments, the aspiration tube carries out the opening to the atmosphere and moves to a predetermined aspiration position with one dropping operation. However, the present invention is not limited thereto. Another aspiration tube may be used such as an aspiration tube of a two-time-piercing type which only carries out opening to the atmosphere with an initial dropping operation and moves to a predetermined aspiration position after rising once and dropping again.

In the above-described embodiments, a blood cell counting apparatus is used as the blood sample processing apparatus. However, a smear preparation apparatus may be used as the blood sample processing apparatus.

In the above-described embodiments, the second rotation process which is performed just before the piercing of the piercer is performed for a shorter time than in other processes. However, all the processes may be performed for the same time period as in the second rotation process which is performed just before the piercing of the piercer.

In the above-described embodiments, a 10-cycle inclining-stirring operation is performed. However, inclining-stirring operations having various numbers of cycles may be performed, and for example, an 8-cycle inclining-stirring operation may be performed.

What is claimed is:

1. A blood sample processing apparatus comprising:
   a container holder configured to secure a sample container that has a closed first end and an open second end sealed with a lid and contains a blood sample inside;
   a rotation driver operably coupled to the container holder to longitudinally rotate the sample container between a first position at which the sample container is positioned upright with the second end thereof held above the first end thereof and a second position at which the sample container is positioned inclined with the first end thereof held at least as high as the second end thereof;
   a sample aspirator configured to aspirate the blood sample in the sample container; and
   a controller programmed to operate the rotation driver to repeat an inclining-stirring operation in cycles that each include a first process, in which the sample container rotates from the first position to the second position, and a second process, in which the sample container rotates from the second position back to the first position, wherein in the first and second processes of each cycle of the inclining-stirring operation, the sample container rotates at a speed between the first and second positions, and
   wherein the controller is further programmed to operate the rotation driver to slow down the speed in the second process in a last cycle of the inclining-stirring operation so that the speed of the second process in the last cycle of the inclining-stirring operation is slower than the speed of a respective first and second processes in each cycle of the inclining-stirring operation performed prior to the second process in the last cycle of the inclining-stirring operation, and that the sample container thereby takes at least 0.8 seconds to rotate back to the first position from the second position in the second process of the last cycle of the inclining-stirring operation and takes shorter than 0.8 seconds in the first and second processes of each cycle of the inclining-stirring operation performed prior to the second process in the last cycle of the inclining-stirring operation, and
   wherein the controller is programmed to operate the sample aspirator to aspirate the blood sample in the sample container after the second process of the last cycle of the inclining-stirring operation is completed.

2. The blood sample processing apparatus of claim 1, wherein the controller is programmed to operate the rotation driver to take about 0.43 seconds to perform the first and second processes of each cycle of the inclining-stirring operation performed prior to the second process in the last cycle of the inclining-stirring operation.

3. The blood sample processing apparatus of claim 1, wherein the controller is programmed to operate the rotation driver to take at least about 1.4 seconds to perform the second process of the last cycle of the inclining-stirring operation, while taking about 0.43 seconds to perform the first and second processes of each cycle of the inclining-stirring operation performed prior to the second process in the last cycle of the inclining-stirring operation.

4. The blood sample processing apparatus of claim 1, wherein the lid comprises a main body that is inserted into the open second end of the sample container, and the main body comprises a bottom surface formed with a concave portion.

5. The blood sample processing apparatus of claim 1,
   wherein the sample aspirator includes an aspiration tube configured to aspirate the blood sample in the sample container and a penetration driver operable to force the aspiration tube to penetrate the lid of the sample container, and
   wherein the controller is programmed to operate the penetration driver to force the aspiration tube to penetrate the lid of the sample container after the second process of the last cycle of the inclining-stirring operation is performed.

6. The blood sample processing apparatus of claim 5, wherein the aspiration tube has a groove in an outer circumferential surface thereof which extends in a longitudinal direction of the aspiration tube.

7. The blood sample processing apparatus of claim 1, wherein the blood sample comprises whole blood.

8. The blood sample processing apparatus of claim 7, further comprising:
   a sample preparation section operable to prepare a measurement sample including the whole blood and a reagent; and
   a detector operable to detect blood cells in the measurement sample.

9. A blood sample processing method comprising:
   stirring a blood sample in a sample container by a rotation driver, the sample container having a closed first end and an open second end sealed with a lid, wherein stirring the blood sample in the sample container comprises longitudinally rotating the sample container between a first position at which the sample container is positioned upright with the second end thereof held above the first end thereof and a second position at which the sample container is positioned inclined with the first end thereof held at least as high as the second end thereof; and
   aspirating the blood sample in the sample container by a sample aspirator after stirring the blood sample in the sample container,
   wherein stirring the blood sample in the sample container comprises operating the rotational driver by a controller to repeat an inclining-stirring operation in cycles that each include a first process, in which the sample container rotates from the first position to the second position, and a second process, in which the sample container rotates from the second position back to the first position, wherein in the first and second processes of each cycle of the inclining-stirring operation, the sample container rotates at a speed between the first and second positions, and wherein stirring the blood sample in the sample container further comprises operating the rotational driver by the controller to slow down the speed in the second process in a last cycle of the inclining-stirring operation so that the speed of the second process in the last cycle of the inclining-stirring operation is slower than the speed of a respective first and second processes in each cycle of the inclining-stirring operation performed prior to the second process in the last cycle of the inclining-stirring operation, and the sample container thereby takes at least 0.8 seconds to rotate back to the first position from the second position in the second process of the last cycle of the inclining-stirring operation and takes shorter than 0.8 seconds in the first and second processes in each cycle of the inclining-stirring operation performed before the second process in the last cycle of the inclining-stirring operation.

10. The blood sample processing method of claim 9, wherein performing the first and second processes of each cycle of the inclining-stirring operation prior to the second process in the last cycle of the inclining-stirring operation takes about 0.43 seconds.

11. The blood sample processing method of claim 9, further comprising penetrating the lid with an aspiration tube after stirring the blood sample, wherein aspirating the blood sample in the sample container is performed after penetrating the lid with an aspiration tube.

12. The blood sample processing method of claim 11, wherein the penetrating the lid with the aspiration tube comprises opening the sample container to ambient atmosphere.

* * * * *